United States Patent
Cheng et al.

(10) Patent No.: US 9,867,857 B2
(45) Date of Patent: Jan. 16, 2018

(54) ACETOBACTER AND GLUCONACETOBACTER STRAINS AND THEIR METABOLITES FOR USE IN INHIBITING XANTHINE OXIDASE

(71) Applicant: Food Industry Research And Development Institute, Hsinchu (TW)

(72) Inventors: Siao-Jhen Cheng, Tainan (TW); Yen-Lin Chen, Hsinchu (TW); Hsun-Yin Hsu, Hsinchu (TW); Kai-Ping Chen, Hsinchu (TW); Chiao-Ming Liao, Hsinchu (TW); Yi-Jen Yech, Hsinchu (TW)

(73) Assignee: Food Industry Research and Development Institute, Hsinchu (TW)

(*) Notice: Subject to any disclaimer, the term of this patent is extended or adjusted under 35 U.S.C. 154(b) by 0 days.

(21) Appl. No.: 14/829,868

(22) Filed: Aug. 19, 2015

(65) Prior Publication Data
US 2016/0051598 A1 Feb. 25, 2016

Related U.S. Application Data

(63) Continuation-in-part of application No. 14/465,094, filed on Aug. 21, 2014, now abandoned.

(51) Int. Cl.
*A61K 35/74* (2015.01)
*A61K 36/06* (2006.01)
*A23L 33/135* (2016.01)

(52) U.S. Cl.
CPC ............ *A61K 35/74* (2013.01); *A23L 33/135* (2016.08); *A61K 36/06* (2013.01); *A23Y 2220/35* (2013.01); *A23Y 2220/37* (2013.01); *A23Y 2220/61* (2013.01); *A23Y 2220/65* (2013.01); *A23Y 2300/55* (2013.01)

(58) Field of Classification Search
CPC ....... A61K 35/74; A61K 36/06; A23L 33/135; A23Y 2220/37; A23Y 2300/55; A23Y 2220/35; A23Y 2220/61; A23Y 2220/65
See application file for complete search history.

(56) References Cited

U.S. PATENT DOCUMENTS

| 3,624,205 | A | | 11/1971 | Falco et al. | |
|---|---|---|---|---|---|
| 3,869,418 | A | * | 3/1975 | Peterson | C08F 271/02 524/460 |
| 6,387,427 | B1 | | 5/2002 | Rekhif et al. | |
| 6,387,654 | B1 | | 5/2002 | Liaw et al. | |
| 2008/0090795 | A1 | | 4/2008 | Aleotti et al. | |
| 2010/0316618 | A1 | | 12/2010 | Tsuboi et al. | |
| 2011/0014168 | A1 | | 1/2011 | Tsubol et al. | |
| 2011/0053224 | A1 | | 3/2011 | Lo et al. | |
| 2013/0330299 | A1 | | 12/2013 | Ranganathan | |
| 2015/0104546 | A1 | * | 4/2015 | Mintus | A23F 5/14 426/93 |

FOREIGN PATENT DOCUMENTS

| CN | 101597583 A | 12/2009 |
|---|---|---|
| CN | 102370859 A | 3/2012 |
| EP | 1649863 A1 | 4/2006 |
| EP | 2457576 A1 | 5/2012 |
| JP | 52015838 A * | 2/1977 |
| JP | 10057046 A | 3/1998 |
| JP | 10201439 A | 8/1998 |
| KR | 2013-0004456 A | 1/2013 |
| KR | 2013-0099653 A | 9/2013 |

OTHER PUBLICATIONS

Ostman, E et al. European Journal of Clinical Nutrition. 2005. 59: 983-988.*
JP 52015838A. Feb. 1977. Derwent English abstract.*
Huang et al "Preparation of Polysaccharides from Wax Gourd" International Journal of Food Sciences and Nutrition vol. 62, pp. 480-483, 2011.
Yang et al "CN 101597583 A" 2009, Full English Translation.
Izumida "Hydroxyakalbne, a Novel Xanthine Oxidase Inhibitor Produced by a Marihe Bacterium, *Agrobacterium Aurantiacum*" The Journal of Antibiotics vol. 50, pp. 916-918. 1997.

* cited by examiner

*Primary Examiner* — Renee Claytor
*Assistant Examiner* — Susan E. Fernandez
(74) *Attorney, Agent, or Firm* — Cesari and McKenna, LLP

(57) ABSTRACT

A method for inhibiting xanthine oxidase and for reducing uric acid levels using a pharmaceutical composition or a food product obtained by culturing *Gluconacetobacter hansenii* or *Acetobacter pasteurianus* in a medium. Also disclosed is a pharmaceutical composition and a food product that each include a metabolite of *Gluconacetobacter hansenii* or *Acetobacter pasteurianus* for reducing uric acid levels in a subject and methods for producing the pharmaceutical composition and the food product.

15 Claims, 2 Drawing Sheets

ACETOBACTER AND GLUCONACETOBACTER STRAINS AND THEIR METABOLITES FOR USE IN INHIBITING XANTHINE OXIDASE

CROSS-REFERENCE TO RELATED APPLICATIONS

The present application is a Continuation-in-Part of U.S. application Ser. No. 14/465,094, which was filed on Aug. 21, 2014. The content of that application is hereby incorporated by reference in its entirety.

BACKGROUND

Field of the Invention

The invention relates to inhibition of xanthine oxidase activity by acetic acid bacteria and their fermentation metabolites.

Background Information

Uric acid is the end product of purine metabolism in the body. A high level of uric acid in the blood leads to the formation and deposition of uric acid crystals in the joints, kidneys, and other organs. A blood uric acid concentration higher than 7 mg/dL is considered to be hyperuricemia.

Hyperuricemia is a common metabolic disorder that is associated with gout, hypertension, cardiovascular disease, diabetes, and kidney disease. An epidemiological survey performed in Taiwan from 1993 to 2008 indicated that the percentage of male and female patients demonstrating hyperuricemia was 21.6% and 9.57%, respectively.

Xanthine oxidase is a key enzyme in the synthesis of uric acid. As a result, inhibition of xanthine oxidase activity can reduce the production of uric acid. Indeed, the xanthine oxidase inhibitor, uricase, is effective for lowering the concentration of uric acid in the blood. Uricase is an enzyme not found in humans. It is typically isolated as a recombinant mammalian protein and administered by IV infusion. As such, it can be expensive to produce and difficult to administer.

Allopurinol is also a xanthine oxidase inhibitor. This compound is administered clinically to lower serum uric acid levels. However, allopurinol has side effects, such as allergic reactions, gastrointestinal discomfort, leukopenia and thrombocytopenia, hepatitis, nephropathy, and 6-mercaptopurine toxicity, which in certain cases can lead to death.

In view of the drawbacks of existing therapies for hyperuricemia, many biopharmaceutical companies focused on the development of new uric acid-lowering agents. For example, Izumida et al., J. Antibiotics 50:916-918, isolated a compound that can lower uric acid levels, namely, hydroxyakalone, from the marine bacterium *Agrobacterium aurantiacum*.

Other microbial species have also been shown to possess uric-acid lowering capability, including strains of *Acetobacter aceti, Acetobacter pasteurianus, Acetobacter peroxydans, Kluyveromyces fragilis, Bacillus subtilis, Lactobacillus fermentum, Lactobacillus pentosus, Lactobacillus gasseri, Lactobacillus oris, Bifidobacterium longum*, and *Saccharomyces cerevisiae*. See, e.g., U.S. Patent Application Publications 2010/0316618, 2011/0014168, and 2013/0330299; European Patent Application Publications 2457576 and 1649863; Chinese Patent Application Publication CN102370859; and Korean Patent Application Publications KR20130099653 and KR20130004456.

The need still exists to develop new xanthine oxidase inhibitors from natural sources which can be easily produced and safely administered.

SUMMARY

To meet this need, a method for reducing uric acid levels in a subject is disclosed. The method includes the steps of culturing an acetic acid bacteria in a medium to form a composition and administering the composition to the subject in an amount effective for reducing uric acid levels. The acetic acid bacteria is *Gluconacetobacter hansenii* or *Acetobacter pasteurianus*.

Also disclosed is a method for inhibiting xanthine oxidase. The method includes the steps of culturing an acetic acid bacteria in a medium to form a composition and contacting the xanthine oxidase with the composition. Again, the acetic acid bacteria is *Gluconacetobacter hansenii* or *Acetobacter pasteurianus*.

Also within the scope of the invention is a method for producing a composition for reducing uric acid levels in a subject. The method includes the steps of inoculating a medium with an acetic acid bacteria and culturing the acetic acid bacteria in the medium. The acetic acid bacteria is *Gluconacetobacter hansenii* or *Acetobacter pasteurianus*.

Additionally, a composition for reducing uric acid levels in a subject is provided. The composition contains a metabolite of an acetic acid bacteria. The acetic acid bacteria is *Gluconacetobacter hansenii* or *Acetobacter pasteurianus*.

Furthermore, a pharmaceutical composition and a food product for reducing uric acid levels in a subject are disclosed.

The pharmaceutical composition contains a metabolite of an acetic acid bacteria and a pharmaceutically acceptable carrier or excipient. The acetic acid bacteria is *Gluconacetobacter hansenii* or *Acetobacter pasteurianus*.

The food product is a vinegar, a health drink, a yogurt, a beverage, an ice cream, sour milk, a biozyme, or a cheese that contains a metabolite of *Gluconacetobacter hansenii* or *Acetobacter pasteurianus*.

The details of one or more embodiments of the invention are set forth in the description, in the drawings, and in the examples below. Other features, objects, and advantages of the invention will be apparent from the detailed description of several embodiments and also from the claims. All publications and patent documents cited herein are incorporated by reference in their entirety.

BRIEF DESCRIPTION OF THE DRAWINGS

The invention description below refers to the accompanying drawings, of which.

DETAILED DESCRIPTION

Figure 1:
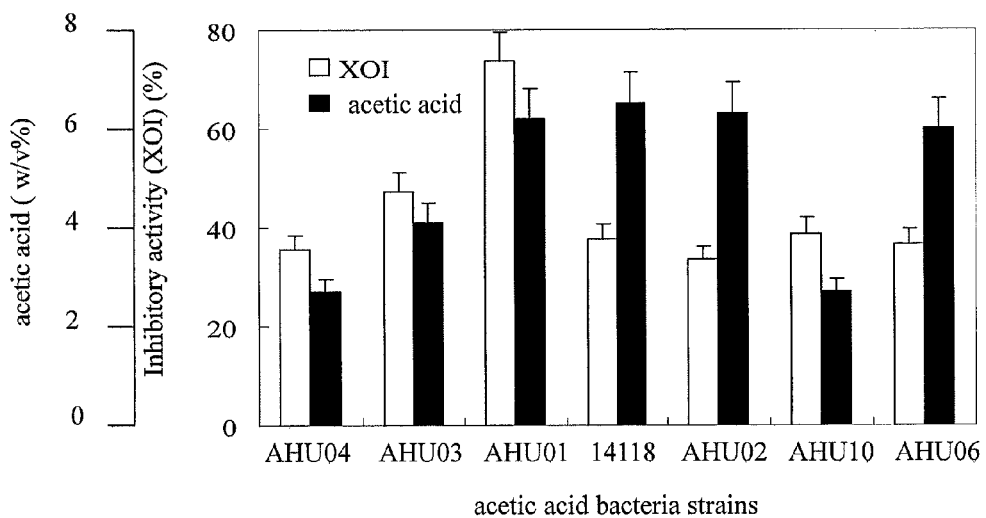
FIG. 1 is a bar graph showing xanthine oxidase inhibitory activity of acetic acid bacteria strains.

As set forth above, a method for reducing uric acid levels in a subject is disclosed that includes a step of culturing the acetic acid bacteria *Gluconacetobacter hansenii* or *Acetobacter pasteurianus* in a medium to form a composition. The acetic acid bacteria can be selected from *Acetobacter pasteurianus* strains AHU01 and AHU02, deposited under Accession Nos. DSM 28893 and DSM 28894, respectively. Alternatively, the *Acetobacter pasteurianus* strains can be strains AHU03 and AHU04. In a particular embodiment, the acetic acid bacteria is *Gluconacetobacter hansenii* strain AHU06, deposited under Accession No. DSM 28902.

The culturing step is carried out in a medium. The medium can be, but is not limited to, M1A broth, a rice extract, a sorghum extract, grape juice, and plum juice. The medium is free of apple juice. In a particular embodiment, the method includes a step of removing the acetic acid bacteria from the medium after culturing and prior to administering the composition.

The composition can be a vinegar or a health drink. In a specific embodiment, the method includes a step of lyophilizing the composition to form a powder.

In an embodiment, the composition is administered orally to the subject. In a specific embodiment, the subject suffers from gout or hyperuricemia.

The amount of the composition administered is effective for reducing uric acid levels in the subject. A skilled artisan can easily determine the effective amount by, e.g., measuring changes in the concentration of uric acid in the blood of the subject.

A method for inhibiting xanthine oxidase is also provided. The method, as mentioned above, requires culturing an acetic acid bacteria in a medium to form a composition. The acetic acid bacteria can be *Gluconacetobacter hansenii* or *Acetobacter pasteurianus*. In an embodiment, the acetic acid bacteria is selected from *Acetobacter pasteurianus* strains AHU01, AHU02, AHU03, and AHU04. In another embodiment, the acetic acid bacteria is *Gluconacetobacter hansenii* strain AHU06.

As set forth above, the culturing step is carried out in a medium. The medium can be, but is not limited to, M1A broth, a rice extract, a sorghum extract, grape juice, and plum juice. The medium is free of apple juice. In a particular embodiment, the method includes a step of removing the acetic acid bacteria from the medium after culturing and prior to contacting the composition with the xanthine oxidase.

In one embodiment, the contacting step can be performed in vitro. For example, a preparation of xanthine oxidase can be placed in a vessel together with the composition. In another embodiment, the contacting step is accomplished by administering the composition orally to a subject having xanthine oxidase.

The method set forth above for producing a composition for reducing uric acid levels in a subject includes, among others, a step of inoculating a medium with an acetic acid bacteria. The acetic acid bacteria is *Gluconacetobacter hansenii* or *Acetobacter pasteurianus*. In one embodiment, the acetic acid bacteria is selected from *Acetobacter pasteurianus* strains AHU01, AHU02, AHU03, and AHU04. In a specific embodiment, the acetic acid bacteria is *Gluconacetobacter hansenii* strain AHU06.

The method also includes a step of culturing the acetic acid bacteria in the medium to form the composition. The medium can be, but is not limited to, M1A broth, a rice extract, a sorghum extract, grape juice, and plum juice. The medium is free of apple juice.

In a particular embodiment, the method includes a step of removing the acetic acid bacteria from the medium after culturing and prior to administering the composition. In a preferred embodiment, the culture density of the acetic acid bacteria prior to the removing step is $1 \times 10^7$ to $1 \times 10^8$ cells/ml.

The composition obtained by culturing the acetic acid bacteria in a medium can be sterilized by methods including but not limited to pasteurization, irradiation, autoclave, and filtration. For example, the composition can be sterilized by filtration through a 0.2 µm filter. In a particularly preferred embodiment, the sterilized liquid broth is first filtered or centrifuged to remove the bacteria and then concentrated.

The composition thus formed can be a food product such as a vinegar or a health drink. In further embodiments, the composition can be a yogurt, a beverage, an ice cream, sour milk, a biozyme (an enzyme mixture extracted from fermented fruits or vegetables), or a cheese.

In a specific embodiment, the method includes a step of lyophilizing the composition to form a powder.

A composition for reducing uric acid levels in a subject is disclosed which contains a metabolite of *Gluconacetobacter hansenii* or *Acetobacter pasteurianus*. As mentioned above the acetic acid bacteria can be selected from *Acetobacter pasteurianus* strains AHU01, AHU02, AHU03, and AHU04. In one embodiment, the acetic acid bacteria is *Gluconacetobacter hansenii* strain AHU06. The composition can be in powder form.

The compositions described above can also contain one or more food ingredients, e.g., a colorant, an acidity regulator, an anticaking agent, an antioxidant, a bulking agent, a carrier, an emulsifier, a flavor enhancer, a glazing agent, a preservative, a stabilizer, a sweetener, a thickener, a nutrient additive, and a flavoring agent.

In a particular embodiment, the composition includes a pharmaceutically acceptable carrier or excipient.

The term "carrier" or "excipient" as used herein refers to any substance, not itself a therapeutic agent, used as a carrier, diluent, adjuvant, or vehicle (i) for delivery of a therapeutic agent to a subject, (ii) for adding to a formulation to improve its handling or storage properties, and/or (iii) to facilitate formation of a dosage unit of the composition into a discrete article such as a capsule or tablet suitable for oral administration.

Suitable carriers or excipients are well known in the art of manufacturing pharmaceutical formulations or food products. Carriers or excipients can include, by way of illustration and not limitation, buffers, diluents, disintegrants, binding agents, adhesives, wetting agents, polymers, lubricants, glidants, substances added to mask or counteract a disagreeable taste or odor, flavors, dyes, fragrances, and substances added to improve appearance of the composition.

Acceptable carriers or excipients include citrate buffer, phosphate buffer, acetate buffer, bicarbonate buffer, stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, cellulosic materials (e.g., cellulose esters of alkanoic acids and cellulose alkyl esters), low melting wax cocoa butter, amino acids, urea, alcohols, ascorbic acid, phospholipids, proteins (e.g., serum albumin), ethylenediamine tetraacetic acid (EDTA), dimethyl sulfoxide (DMSO), sodium chloride or other salts, liposomes, mannitol, sorbitol, glycerol or powder, polymers (e.g., polyvinyl-pyrrolidone, polyvinyl alcohol, and polyethylene glycols), and other pharmaceutically acceptable materials. The carrier does not destroy the pharmacological activity of the therapeutic agent and is non-toxic when administered in doses sufficient to deliver a therapeutic amount of the agent.

In another embodiment, the composition can include, in addition to the metabolite of the acetic acid bacteria, probiotic microorganisms including but not limited to *Lactobacillus* spp., *Bifidobacterium* spp., and *Saccharomyces* spp. For example, one or more of *Lactobacillus fermentum*, *Lactobacillus pentosus*, *Lactobacillus gasseri*, *Lactobacillus oris*, *Bifidobacterium longum*, and *Saccharomyces cerevisiae* can be included in the composition. In a particular aspect, the composition contains one or more of the above-mentioned probiotic microorganisms and a metabolite of an acetic acid bacteria selected from *Acetobacter pasteurianus* strains AHU01, AHU02, AHU03, AHU04, and *Gluconacetobacter hansenii* strain AHU06.

Without further elaboration, it is believed that one skilled in the art can, based on the disclosure herein, utilize the present invention to its fullest extent.

The following specific examples are, therefore, to be construed as merely descriptive, and not limitative of the remainder of the disclosure in any way whatsoever.

EXAMPLES

Example 1: Acetic Acid Bacteria Produce a Xanthine Oxidase Inhibitory Activity

Fifty-one acetic acid bacteria strains were separately inoculated onto M1A plates (2.5% mannitol, 0.5% yeast extract, 0.3% peptone, and 2% agar) and the plates incubated for 2 days at 30° C. to form colonies.

Xanthine oxidase inhibitory activity was measured as follows. First, 10 µl of each strain was scraped from the M1A plate and added to a well in a 96 well plate. Then 150 µl of 50 mM phosphate-buffered saline (PBS) and 80 µl of 150 µM xanthine was added to each well. An initial absorbance value at 290 nm ($OD_{before}$) was determined before adding 10 µl of xanthine oxidase (0.1 U) into each well. After incubating the plate at 25° C. for 30 min., the absorbance value was measured again at 290 nm ($OD_{after}$). The xanthine oxidase inhibitory activity of each sample was calculated according to the following formula:

$$XOI(\%) = \frac{100 \times [1 - (OD_{after} - OD_{before})]}{(\text{Blank } OD_{after} - \text{Blank } OD_{before})}$$

The results are shown in FIG. 1. Among the 51 distinct acetic acid bacterial strain examined, only seven strains inhibited xanthine oxidase by more than 30%. In particular, *Acetobacter pasteurianus* strain AHU01 inhibited xanthine oxidase activity by 73.6%.

Applicants deposited *Acetobacter pasteurianus* strains AHU01 and AHU02 on Jun. 5, 2014 under the terms of the Budapest Treaty with the International Strain Depositary Leibniz Institute DSMZ-German Collection of Microorganisms and Cell Culture, Inhoffenstr. 7 B, D-38124 Braunschweig GERMANY. *Acetobacter pasteurianus* strains AHU01 and AHU02 were assigned Accession Nos. DSM 28893 and DSM 28894, respectively. Applicants also deposited on Jun. 5, 2014 *Gluconacetobacter hansenii* strain AHU06 in the above repository under Accession No. DSM 28902.

Example 2: Effect of Media on Acetic Acid Bacteria Xanthine Oxidase Inhibition

Figure 2:
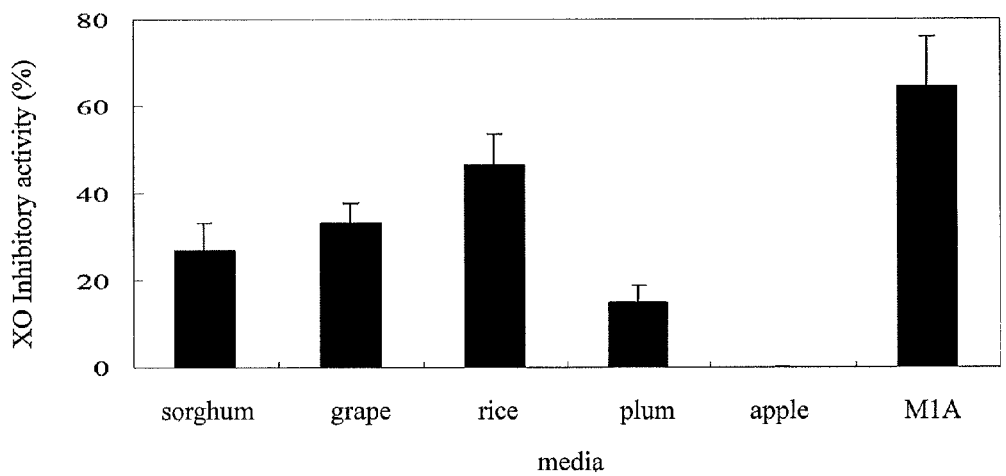
FIG. 2 is a bar graph showing xanthine oxidase inhibitory activity of *Acetobacter pasteurianus* strain AHU02 grown in different media.

*Acetobacter pasteurianus* strain AHU02 was inoculated onto M1A plates and cultured at 30° C. for 4 days. Each plate was washed with 7 ml of sterile M1A seed broth. The seed broth containing cells (1 ml) was inoculated into 50 ml of various media in a 250 ml triangular flask. The inoculated media were incubated at 30° C. with shaking at 125 rpm for 7 days. Samples of each media was assayed for xanthine oxidase inhibition as described above. The results are shown in FIG. 2.

*Acetobacter pasteurianus* strain AHU02 produced the highest level of xanthine oxidase inhibitory activity, reaching 60% inhibition. By contrast, no inhibition of xanthine oxidase activity was detected after growing *Acetobacter pasteurianus* strain AHU02 in apple juice. Culturing *Acetobacter pasteurianus* strain AHU02 in sorghum, grape juice, rice extract and plum juice resulted in intermediate levels of inhibitory activity ranging from 15% to 50%.

Figure 3:
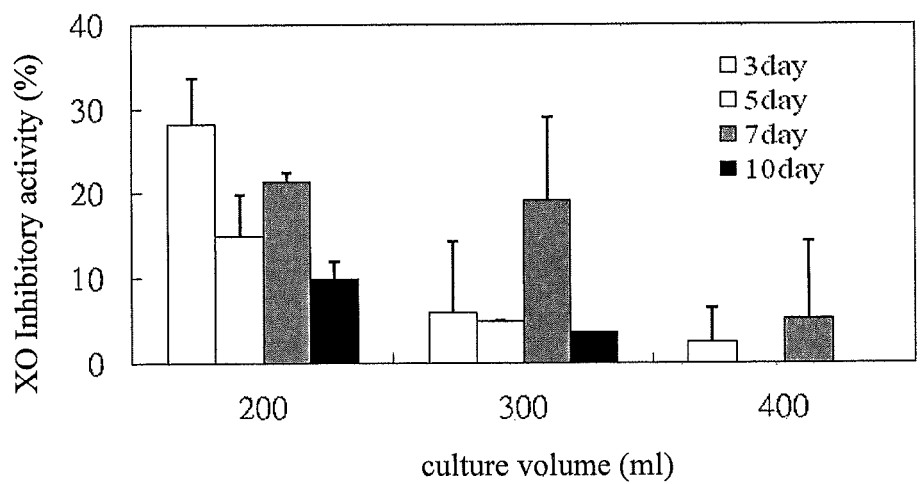
FIG. 3 is a bar graph showing xanthine oxidase inhibitory activity of *Acetobacter pasteurianus* strain AHU02 grown in different volumes of media for specific periods of time.

Example 3: Effect of Culturing Time and Volume on Acetic Acid Bacteria Xanthine Oxidase Inhibition A seed broth containing *Acetobacter pasteurianus* strain AHU02 was prepared as described in Example 2 above. Seed broth was added at 2% v/v to 200, 300, and 400 ml of SPS medium (1% sucrose, 1% peptone, 1% soy peptone, and 0.2% sodium nitrate) in a 1 L triangular shaker flask and incubated with shaking at 125 rpm for 3-10 days at 30° C. Xanthine oxidase inhibition was measured as set forth in Example 1 supra. The results are shown in FIG. 3.

*Acetobacter pasteurianus* strain AHU02 grown in a culture volume of 200 ml produced the highest level of xanthine oxidase inhibitory activity at each time point as compared to this strain grown in 300 ml or 400 ml of media. It is known that the smaller culture volume results in more efficient oxygenation of the media during culture. Without being bound by theory, it is likely that efficient production of xantine oxidase inhibitory activity by *Acetobacter pasteurianus* requires a high level of oxygen.

The highest level of xanthine oxidase inhibitory activity was obtained after 3 days of culturing *Acetobacter pasteurianus* strain AHU02 in a 200 ml volume. This level decreased upon prolonged culturing, falling off by nearly 65% after 10 days of culture. A similar reduction in xanthine oxidase inhibitory activity over time was observed in the 300 ml and 400 ml cultures.

Example 4: Effect of Glucose Concentration on Production of Xanthine Oxidase Inhibitory Activity by Acetic Acid Bacteria A seed broth containing *Acetobacter pasteurianus* strain AHU01 was prepared as described in Example 2 above. In a 250 ml triangular flask, 0.5 ml of the seed broth was inoculated into 50 ml of media each containing a different concentration of glucose ranging from 8% to 16% (w/v). In addition to glucose, the media contained 1.5% soy peptone and 3% yeast extract. The cultures were incubated at 30° C. with shaking at 150 rpm for 7 days.

Xanthine oxidase inhibitory activity was measured by HPLC by the following procedure. In a reaction tube, 880 µl of xanthine (50 µg/ml in 100 mM PBS) and 40 µl of 50 mM PBS or 40 µl of the culture supernatants were premixed, and 80 µl of xanthine oxidase (0.1 U) was added to initiate the reaction. The reaction was incubated at 30° C. for 30 min., after which an equal volume of absolute ethanol was added to terminate the reaction. The terminated reaction was filtered through a 0.22 µm membrane filter and the content of xanthine in the reactions was analyzed by HPLC. Xanthine oxidase inhibitory activity of the samples was calculated as follows:

$$XOI(\%) = \frac{100 \times [\text{xanthine}]_{initial} - [\text{xanthine}]_{after\ sample}}{[\text{xanthine}]_{initial} - [\text{xanthine}]_{after\ control}}$$

The results are shown in Table 1 as follows:

TABLE 1

Inhibition of xanthine oxidase activity

| glucose concentration | xanthine oxidase inhibition |
|---|---|
| 8[a] | 32.74[b] |
| 10 | 41.97 |
| 12 | 55.84 |
| 16 | 68.12 |

[a]values expressed as w/v % of glucose in the media.
[b]values expressed as percentage inhibition of xanthine oxidase activity.

A clear correlation exists between the glucose content of the growth media and the level of xanthine oxidase activity produced by *Acetobacter pasteurianus* grown in the media.

Example 5: Treatment of Experimental Uricemia

*Acetobacter pasteurianus* strain AHU01 was inoculated onto an M1A plate and cultured for 2 days at 30° C. The plate was washed with 7 ml of sterile water as seed broth. 0.5 ml of the seed broth was inoculated into 50 ml of a custom media (1% soy peptone, 0.2% yeast extract, 3% glucose, 0.2% malt extract, and 3% fructose) in a 250 ml triangular flask and incubated with shaking at 150 rpm for 7 days at 30° C. The medium was then collected and centrifuged at 3000 rpm for 15 minutes. Following centrifugation, the supernatant was collected, lyophilized, and freeze-dried to form a solid fermentation product for use in animal experiments.

ICR mice were used as experimental animals. Potassium oxonate, a uricase inhibitor, was used to induce a high level of uric acid in the serum of the mice. Mice were fasted for one hour and then fed saline or potassium oxonate (400 mg/kg) via a feeding tube. After one hour, potassium oxonate-treated mice were fed saline, allopurinol (10 mg/kg), or the *Acetobacter pasteurianus* strain AHU01 fermentation product (150 mg or 200 mg resuspended in saline per mouse) prepared as described above. Ten animals were used for each experimental group and for the control group. The animals were sacrificed after one hour and the level of uric acid in their serum was analyzed. The results are shown in Table 2 below.

TABLE 2

A fermentation product of *Acetobacter pasteurianus* strain AHU01 can reduce serum uric acid levels in experimental animals.

| Experimental group[a] | serum uric acid concentration |
|---|---|
| saline control | 3.51 ± 0.02 mg/dL |
| potassium oxonate (400 mg/kg) | 4.91 ± 0.08 mg/dL |
| potassium oxonate + allopurinol (10 mg/kg) | 2.82 ± 0.28 mg/dL |
| potassium oxonate + 150 mg fermentation product | 2.98 ± 0.13 mg/dL |
| potassium oxonate + 200 mg fermentation product | 2.94 ± 0.12 mg/dL |

[a]mice (N = 10 per condition) fed saline or the compounds indicated in a total volume of 200 μl Other Embodiments All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, a person skilled in the art can easily ascertain the essential characteristics of the present invention, and without departing from the spirit and scope thereof, can make various changes and modifications of the present invention to adapt it to various usages and conditions. Thus, other embodiments are also within the claims.

The invention claimed is:

1. A pharmaceutical composition for reducing uric acid levels in a subject, the composition comprising dextrin and a culture of an acetic acid bacteria in a medium that contains glucose, soy peptone, and yeast extract, wherein the acetic acid bacteria is *Acetobacter pasteurianus* strain AHU01, deposited under Accession No. DSM 28893, and the pharmaceutical composition is in lyophilized form.

2. The composition of claim 1, further comprising at least one microorganism selected from the group consisting of *Lactobacillus* spp., *Bifidobacterium* spp., and *Saccharomyces* spp.

3. The composition of claim 2, wherein the at least one microorganism is *Lactobacillus fermentum*, *Lactobacillus pentosus*, *Lactobacillus gasseri*, *Lactobacillus oris*, *Bifidobacterium longum*, or *Saccharomyces cerevisiae*.

4. A food product for reducing uric acid levels in a subject, the food product comprising in lyophilized form an acetic acid bacteria and dextrin, wherein the acetic acid bacteria is *Acetobacter pasteurianus* strain AHU01, deposited under Accession No. DSM 28893, and the food product is a vinegar, a health drink, a yogurt, a beverage, an ice cream, sour milk, or a cheese.

5. The food product of claim 4, further comprising a food ingredient.

6. The food product of claim 5, wherein the food ingredient is one or more of a colorant, an acidity regulator, an anticaking agent, an antioxidant, a bulking agent, a carrier, an emulsifier, a flavor enhancer, a glazing agent, a preservative, a stabilizer, a sweetener, a thickener, a nutrient additive, and a flavoring agent.

7. The food product of claim 6, further comprising at least one microorganism selected from the group consisting of *Lactobacillus* spp., *Bifidobacterium* spp., and *Saccharomyces* spp.

8. The food product of claim 7, wherein the at least one microorganism is *Lactobacillus fermentum*, *Lactobacillus pentosus*, *Lactobacillus gasseri*, *Lactobacillus oris*, *Bifidobacterium longum*, and *Saccharomyces cerevisiae*.

9. The food product of claim 4, further comprising at least one microorganism selected from the group consisting of *Lactobacillus* spp., *Bifidobacterium* spp., and *Saccharomyces* spp.

10. The food product of claim 9, wherein the at least one microorganism is *Lactobacillus fermentum*, *Lactobacillus pentosus*, *Lactobacillus gasseri*, *Lactobacillus oris*, *Bifidobacterium longum*, or *Saccharomyces cerevisiae*.

11. A method for reducing uric acid levels in a subject, the method comprising identifying a subject in need of reduced uric acid levels and administering the pharmaceutical composition of claim 1 to a subject in need thereof in an amount effective for reducing uric acid levels.

12. The method of claim 11, wherein the subject suffers from gout or hyperuricemia.

13. The method of claim 12, wherein the pharmaceutical composition further comprises at least one microorganism selected from the group consisting of *Lactobacillus fermentum*, *Lactobacillus pentosus*, *Lactobacillus gasseri*, *Lactobacillus oris*, *Bifidobacterium longum*, and *Saccharomyces cerevisiae*.

14. A method for reducing uric acid levels in a subject, the method comprising identifying a subject in need of reduced uric acid levels and administering the food product of claim 4 to a subject in need thereof in an amount effective for reducing uric acid levels.

15. The method of claim 14, wherein the food product further comprises at least one microorganism selected from the group consisting of *Lactobacillus fermentum*, *Lactobacillus pentosus*, *Lactobacillus gasseri*, *Lactobacillus oris*, *Bifidobacterium longum*, and *Saccharomyces cerevisiae*.

* * * * *